United States Patent [19]

Schmid

[11] 4,004,907
[45] Jan. 25, 1977

[54] ARYLISOTHIOCYANATE FOR THE REGULATION OF PLANT GROWTH

[75] Inventor: Wolfgang Schmid, Therwil, Switzerland

[73] Assignee: Ciba-Geigy Corporation, Ardsley, N.Y.

[22] Filed: Oct. 15, 1975

[21] Appl. No.: 622,596

[30] Foreign Application Priority Data

Oct. 22, 1974 Switzerland ............... 14102/74

[52] U.S. Cl. .................................. 71/72; 260/454; 71/104

[51] Int. Cl.² ................... A01N 9/12; C07C 161/04

[58] Field of Search ................ 260/454; 71/104, 72

[56] References Cited

UNITED STATES PATENTS 2,263,386  11/1941  Hester ............................. 260/454
3,420,892  1/1969  Martin et al. ..................... 260/454

OTHER PUBLICATIONS

Collect. Czech. Chem. Commun. 38, [1973], pp. 3852–3856.

Chem. Abst. 82, (1975), p. 31126t.

*Primary Examiner*—Lewis Gotts
*Assistant Examiner*—D. R. Phillips
*Attorney, Agent, or Firm*—Harry Falber

[57] ABSTRACT

New arylisothiocyanates corresponding to the formula

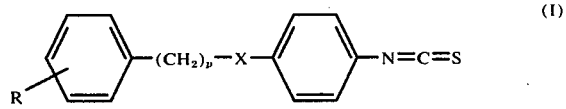

wherein
R represents alkyl, alkoxy or halogen
X represents oxygen or sulfur and
p represents an integer of from 2 to 5 are disclosed.

They can be used for the regulation of plant growth especially for the dessication and defoliation of unlignified parts of plants above the soil.

9 Claims, No Drawings

ARYLISOTHIOCYANATE FOR THE REGULATION OF PLANT GROWTH

The present invention relates to arylisothiocyanates, to processes for their production, as well as to compositions and processes for the defoliation and desiccation of unlignified parts of plants above the soil by use of the new arylisothiocyanates of the following formula I

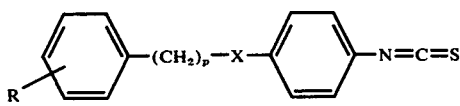

wherein
R represents hydrogen, alkyl, alkoxy or halogen,
X represents oxygen or sulphur, and
P represents an integer from 2 to 5.

By alkyl and alkoxy are meant lower radicals having 1 to 4 carbon atoms, such as the methyl, ethyl, n-propyl, isopropyl, n-butyl, isobutyl, sec-butyl or tert-butyl radical or the corresponding alkoxy radicals. Halogen denotes fluorine, chlorine or bromine.

The new active substances of the formula I are obtained by a process in which an aniline derivative of the formula II

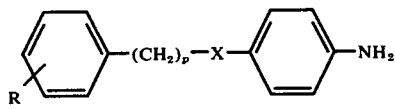

a. is reacted with a thiocarbonic acid derivative of the formula

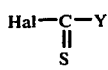

wherein Hal represents chlorine or bromine and Y denotes chlorine, bromine or a dialkylamino group; or
b. is reacted with a sulphide of the formula

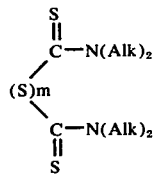

wherein Alk represents a lower alkyl radical having at most 4 carbon atoms; or
c. is reacted with pentathio-dipercarbonic acid-bis-(trihalogenoalkyl)-esters; or
d. is reacted with phosgene and phosphorus pentasulphide in a solvent or diluent inert to the reactants; or
e. is converted with benzoylisothiocyanate into the corresponding thiourea, and this is decomposed by pyrolysis in the presence of a solvent inert to the reactants, preferably in an aromatic hydrocarbon or halogenated hydrocarbon, or in the presence of acids or acid anhydrides; or
f. is converted with carbon disulphide in the presence of an inorganic base or of an amine into the corresponding dithiocarbamic acid salts, and these are then dehydrosulphurised; or
g. is reacted with carbon disulphide in the presence of carbodiimides and of a tertiary amine; or
h. is reacted with ammonium rhodanide in the presence of gaseous hydrogen chloride.

The processes are performed in the presence of solvents or dilvents inert to the reactants. In processes according to the invention there can be used, for example: aliphatic and aromatic hydrocarbons; aliphatic and aromatic halogenated hydrocarbons; ethers and ethereal compounds such as dioxane and tetrahydrofuran; ketones; amides such as dimethylformamide; or water or mixtures of such solvents with each other or with water.

In the production of isothiocyano compounds of the formula I with the aid of the methods given under a) to h), there are used temperatures of between −20° and 150° C, preferably between −10° and +30° C; and with the use of a dialkylthiocarbamoyl halide such as diethylthiocarbamoyl chloride, or with decomposition by pyrolysis according to Method e), or with the reaction according to Method h), there are used higher temperatures of between 40° and 200° C.

The formation of the isothiocyano group is effected by methods known per se: reactions of amines with thiophosgene (a) are described in Houben-Weyl, 4th edition, Vol. 9, page 876 (1955); the use of acid-binding agents by O. E. Schultz in Arch. Pharm. 295, 146–151 (1962); the reaction of amines with N,N-diethylthiocarbamoyl chloride (a) has been described in Journal Org. Chem. 30, 2465 (1965), with bis-thiocarbamoyl sulphides (b) by F. H. Marquardt in Helv. Chim. Acta 49, 1716 (1966); and the reaction of amines with pentathiodipercarbonic acid-bis-(trihalogenoalkyl)-esters (c) by R. Gottfried in Angew. Chemie 78, 985 (1966); and with phosgene and phosphorus pentasulphide in Houben-Weyl, 4th Edition, Vol. 9, page 867 and following.

The solvents preferably employed for the reactions given under (d) and (e) are o-dichlorobenzene and chlorobenzene; also suitable however are other dichlorobenzenes, toluene, xylenes, cumol, etc.. The decomposition by pyrolysis of thioureas (e) is performed in the manner described by J. N. Baxter et al. in J. Chem. Soc. (1956), page 659 and following. The thioureas are produced according to Org. Synthesis III, 735 (1955).

In the production of dithiocarbamic acid salts (f), the inorganic bases used are, for example, the hydroxides, oxides and carbonates of alkali metals and alkaline-earth metals, as well as ammonium hydroxide; the amines used are, for example, trialkylamines, pyridine base or ammonia [See C. A. 70, 3389 q (1969)]. The dehydrosulphurisation (c) can be performed oxidatively with metal salts (Brit. Pat. No. 793,802, Dutch Pat. No. 81,326), e.g. with lead, copper, zinc or iron-(III) salts, iodine, alkali metal hypochlorides and alkali metal hypochlorites, preferably with those of potassium and sodium (French Pat. No. 1,311,855); also with suitable acid chlorides such as phosgene and phosphorus oxychloride (D. Martin et. al. Chem. Ber. 98, 2425–2426 (1965), as well as with elementary chlorine and ammonium sulphide (DAS 1,192,139) or chloramine T (Brit. Pat. No. 1,024,913).

Arylisothiocyanates of the formula I are produced, for example, by reacting an aniline derivative of the formula II either with thiophosgene in the presence of a suitable organic solvent or diluent or water, or with ammonium rhodanide in the presence of gaseous hydrogen chloride.

Aniline derivatives of the formula II and their immediate precursors, the nitro compounds, are in some cases known or can be produced by known methods (see J. Am. Chem. Soc. 45, 2402, 2406, 2407, J. Am. Chem. Soc. 72, 2856–2859 (1950).

Following examples illustrate the production of the compounds of the invention. In the following Table there are listed further compounds which are obtained in an analogous manner. Temperature values are given in degrees Centigrade.

EXAMPLE 1 a. 5.6 g of anhydrous potassium hydroxide is dissolved in 200 ml of anhydrous ethanol. To this solution there are added 15.5 g of 4-nitrothiophenol and then 19.9 g of 3-phenyl-propyl bromide; the reaction mixture is refluxed for 2 hours and, after cooling, poured with stirring into 500 ml of ice-water. The resulting 4-(3'-phenylpropylthio)-nitrobenzene crystallises out and melts at 66°–68° after recrystallisation from ethanol.

b. 90 g of 4-(3'-phenyl-propylthio)-nitrobenzene is catalytically hydrogenated in 300 ml. of dimethylformamide with Raney nickel. After completion of the hydrogen absorption and removal of the catalyst and the solvent, there is obtained 4-(3'-phenyl-propylthio)-aniline as an oily residue, which can be used without purification in the next reaction stage.

c. 6.4 g of the 4-(3'-phenyl-propylthio)-aniline obtained under (b) is dissolved in 50 ml of 1,2-dichlorobenzene, and the solution is saturated at room temperature, with stirring, with anhydrous hydrogen chloride. There is subsequently added 2.5 g of ammonium rhodanide, and the whole is heated, with the continuous introduction of hydrogen chloride, for 6 hours at 130° to 140°. The undissolved constituents are filtered off, and the filtrate is chromatographed through silica gel with 1,2-dichlorobenzene as the eluant. There is obtained pure 4-(3'-phenyl-propylthio)-phenyl-isothiocyanate having a refractive index of $n_D^{25} = 1.6672$ (= Compound No. 1).

EXAMPLE 2 a. 73 g of 4-nitrophenol, 200 ml of N,N-dimethylacetamide, 38 g of potassium carbonate and 99.5 g of 3-phenylpropyl bromide are placed together and heated in an oil bath for 16 hours at 150°. The cooled mixture is poured, with stirring, into 2 liters of ice-water, the precipitated crystalline product is filtered off, and chromatographed through silica gel with methylene chloride as the eluant. The pure 4-(3'-phenyl-propoxy)-nitrobenzene has a melting point of 78°–79°.

b. 99 g of 4-(3'-phenyl-propoxy)-nitrobenzene is dissolved in 2000 ml of methanol and hydrogenated with Raney nickel until the absorption of hydrogen is completed. The catalyst is filtered off and the filtrate is concentrated by evaporation to obtain, as a crystalline residue, 4-(3'-phenylpropoxy)-aniline having a melting point of 55°–57°.

c. 73.2 g of thiophosgene is stirred with 1000 ml of water and 500 g of ice. There is then added dropwise at 0° to 5° a solution of 133.2 g of 4-(3'-phenyl-propoxy)-aniline in 200 ml of dioxane. Stirring is continued for a further half hour; to the reaction mixture there is added 300 ml of methylene chloride and the whole is subsequently neutralized, with cooling, with sodium hydrogen carbonate. The methylene chloride phase is dried over sodium sulphate and then chromatographed through silica gel with methylene chloride as the eluant. The resulting pure 4-(3'-phenyl-propoxy)-phenyl-isothiocyanate melts at 51° – 53° (= Compound No. 2).

EXAMPLE 3 a. 75 g of 4-chloronitrobenzene in 300 ml of ethanol is heated to 70°. At this temperature there is then added dropwise 27 g of anhydrous potassium hydroxide and 65.9 g of 2-phenylethyl mercaptan in 250 ml of ethanol; the reaction mixture is refluxed for one hour and is then poured, with stirring into 1.5 liters of ice-water. The precipitated oil is extracted with methylene chloride, and the methylene chloride phases are dried over sodium sulphate. After purification through silica gel with methylene chloride as the eluant, there is obtained 4-(2'-phenyl-ethylthio)-nitrobenzene having a melting point of 35° – 37°.

b. 86 g of 4-(2'-phenyl-ethylthio)-nitrobenzene is dissolved in 900 ml of methanol and catalytically hydrogenated with Raney nickel. After completion of the absorption of hydrogen, the catalyst is filtered off and the filtrate is concentrated by evaporation. There is obtained 4-(2'-phenyl-ethylthio)-aniline as oily residue, which is used without purification in the next reaction stage.

c. 25.2 g of the 4-(2'-phenyl-ethylthio)-aniline produced under b) is dissolved in 80 ml of dioxane. This solution is added dropwise in the course of 15 minutes to a mixture of 12.6 g of thiophosgene in 70 ml of dioxane, with the temperature rising to 40°. The solution is stirred for about a further 15 hours; it is then poured into ice-water and extracted with methylene chloride. The methylene chloride phases are dried over sodium sulphate, the solvent is evaporated off and the residue chromatographed through silica gel with a mixture of hexane/ethyl acetate 95:5. There is obtained pure 4-(2'-phenyl-athylthio)-phenylisothiocyanate having a refractive index of $n_D^{24} = 1.685$ (= Compound No. 3).

| No. | Compound | Physic. data |
|---|---|---|
| 4 | 4-(5'-phenyl-pentylthio)-phenyl-isothiocyanate | $n_D^{24} = 1.649$ |
| 5 | 4-(2'-phenyl-ethoxy)-phenylisothiocyanate | $n_D^{25} = 1.6412$ |
| 6 | 4-(4'-phenyl-butoxy)-phenylisothio cyanate | m.p.: 40–41° |
| 7 | 4-(5'-phenyl-pentyloxy)-phenyliso-thiocyanate | m.p.: 39–41° |
| 8 | 4-[3'-(4-fluorophenyl)-propoxy]-phenylisothiocyanate | m.p.: 63–65° |
| 9 | 4-[3'-(4-chlorophenyl)-propoxy]-phenylisothiocyanate | m.p.: 63–65° |
| 10 | 4-[3'-(4-tolyl)-propoxy]-phenyliso-thiocyanate | m.p.: 53–55° |
| 11 | 4-[3'-(4-chlorophenyl)-propylthio]-phenylisothiocyanate | m.p.: 63–64° |
| 12 | 4-[3'-(4-fluorophenyl)-propylthio-phenylisothiocyanate | m.p. 43–44° |
| 13 | 4-(7'-phenyl-heptylthio-)phenyl-isothiocyanate | $n_D^{20} = 1.5935$ |

The active substances of the formula I are excellently suitable for the regulation of defoliation and desiccation of unlignified parts of plants above the soil. These active substances or compositions containing them are particularly valuable for the removal of the foliage of a wide variety of cultivated plants. The plant itself and likewise the fruit or other crops are not damaged; the after-ripening necessary in many cases thus occurs without impairment. The active substances produce no morphological changes which would result in the withering of the plant. The action differs therefore from that of a herbicidal active substance. The compounds of the invention can therefore also be used for the treatment of plant material intended for seed production and for transportation.

The extent of the action is dependent on a variety of factors: it is dependent particularly on the time of application with regard to the stage of development of the plants, and on the applied concentration. Cultivated crops, such as cotton, leguminosae, sorghum, soya bean, potatoes, grape vines, etc., are mostly treated shortly before harvesting. The foliage withers immediately after application, and falls or dries within a short space of time. Fruits and other crops are consequently exposed and thus rendered easily accessible for manual or mechanical harvesting. As a result of the rapid withering of the foliage, a contamination of the crops by green leaf-parts is moreover prevented, and likewise an infection of the ripe or ripening fruits by pests present on the leaves (e.g. insects or red spider mites, and micro-organisms, e.g. fungi, bacteria and viruses) is avoided.

Compounds that have proved particularly effective are those of formula Ia

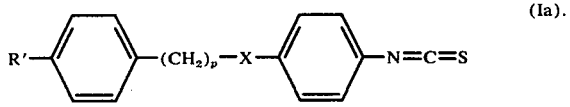

(Ia).

In this formula, the symbols p and X have the meanings given under the formula I; R' represents hydrogen, methyl, methoxy or halogen.

The effectiveness of the arylisothiocyanates of the invention is confirmed by the following tests:

1. Cotton plants having ripe capsules (60% open capsules) are sprayed with aqueous emulsions of the active substances, obtained from 25% emulsion concentrates (plot size about 20 square metres, one repeat, climate: moist-warm). The test results are assessed after 14 days on the basis of the percentage fall of leaves produced by the treatment.

2. The active substances are applied either (a) as a 0.5% aqueous suspension (obtained from a 25% emulsion concentrate) or (b) as a 10% pulverulent concentrate to about 20 cm high cotton plants shortly before appearance of the 3rd leaf. In each case only the surface of the leaf and the petiole of the cotyledons are treated. The plants are then allowed to stand in a greenhouse at 24° to 26° with 45 to 60% relative humidity. The test is evaluated after 3, 7 and 14 days.

3. Soya bean, green pea, bush bean, lucerne, red clover and potato plants, grown in plastics pots, are sprayed until dripping wet, in the one case about 2 weeks after sowing and in the other case about 4 weeks after sowing, with aqueous active-substance dispersions (obtained from 25% emulsion concentrates or from 25% wettable powders) in various concentrations. An evaluation of the test results is made 3, 7 and 14 days after application by visual assessment of necrosis or desiccation, defoliation and new sprouting.

In the tests 1 to 3, the arylisothiocyanates of the formula I according to the invention exhibited a very good defoliating and desiccating action; the compound to be emphasized is 4-(3'-phenyl-propoxy)-phenylisothiocyanate, which with only very small applied amounts produces an almost quantitative defoliation and desiccation.

The compositions according to the invention are produced in a manner known per se by the intimate mixing and/or grinding of active substances of the general formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates and homogeneous granulates;

water-dispersible active-substance concentrates: wettable powders, pastes and emulsions;

liquid preparations: solutions.

The solid (dusts, (dists, scattering agents and granulates) are produced by the mixing of the active substances with solid carriers. Suitable carriers are, e.g., kaolin, talcum, bole, loess, chalk, limestone, ground limestone, attapulgite, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to approx. 0.1 mm; for scattering agents approx. 0.075 to 0.2 mm; and for granulates 0.2 mm or coarser.

The concentration of active substance in the solid preparations is 0.5 to 80%.

It is possible to add to these mixtures also additives stabilising the active substance, and/or nonionic, anionactive and cation-active substances which improve, e.g., the adhesiveness of the active substances on plants and parts of plants (adhesives and agglutinants), and/or ensure better wettability (wetting agents) as well as dispersibility (dispersing agents). Suitable adhesives are, for example, olein/lime mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, lignin-sulphonic acid, the alkali metal salts and alkaline-earth metal salts therof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates, are agents which can be diluted with water to obtain any desired concentration. They consist of active substance, carrier, optionally additives stabilising the active substance, surface-active substances, and anti-foaming agents and, optionally, solvents. The concentration of active substance in these preparations is 5 – 80%.

The wettable powders and pastes are obtained by the mixing and grinding of the active substances with dispersing agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali metal salts, ammonium salts and alkaline-earth metal salts of ligninsulphonic acid, also alkylarylsulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ethers, the sodium salt of oleyl methyl tauride, ditertiary acetylene glycols, dialkyl dilauryl ammonium chloride, and fatty acid alkali-metal and alkaline-earth metal salts.

Suitable anti-foaming agents are, e.g., silicones.

The active substances are so mixed, ground, sieved and strained with the above-mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, benzene, xylenes, toluene, dimethylsulphoxide, N,N,-dialkylated amides, N-oxides of amines, especially trialkylamines, and mineral oil fractions boiling in the range of 120° to 350° C. The solvents must be practically odourless, nonphytotoxic, inert to the active substances and not readily combustible.

Furthermore, the agents according to the invention can be used in the form of solutions. For this purpose, the active substance, or several active substances, of the general formula I is dissolved in suitable organic solvents, solvent mixtures, water, or mixtures of organic solvents with water. As organic solvents, it is possible to use aliphatic and aromatic hydrocarbons, their chlorinated derivatives, alkylnaphthalenes, mineral oils on their own or in admixture with each other. The solutions should contain the active substances in a concentration of 1 to 20%.

These solutions can be applied either by means of a propellent gas (as spray), or by means of special sprayers (as aerosol).

Other biocidal active substances or agents can be mixed with the described compositions of the invention. For the broadening of their sphere of action, the new compositions can for example contain, in addition to the stated compounds of the general formula I, insecticides, fungicides, bactericides, fungistatics, bacteriostatics or nematocides. The compositions of the invention may also contain fertilisers, trace elements, etc..

Preparations of the new active substances of the general formula I are described in the following. Parts are given as parts by weight.

Wettable powders

The following constituents are used to produce (a) a 40%, (b) and (c) a 25% and (d) a 10% wettable powder:

a. 40 parts of Active Substance No. 2; 5 parts of sodium lignin sulphonate, 1 part of sodium dibutylnaphthalene sulphonate; 54 parts of silicic acid;

b. 25 parts of Active Substance No. 1; 4.5 parts of calcium lignin sulphonate; 1.9 parts of Champagne chalk/hydroxyethyl cellulose mixture (1:1); 1.5 parts of sodium dibutyl naphthalene sulphonate; 19.5 parts of silicic acid; 19.5 parts of Champagne chalk; 28.1 parts of kaolin;

c. 25 parts of Active Substance No. 3; 2.5 parts of isooctylphenoxy-polyoxyethyleneethanol; 1.7 parts of Champagne chalk/hydroxyethyl cellulose mixture (1:1); 8.3 parts of sodium aluminium silicate; 16.5 parts of kieselguhr; 46 parts of kaolin;

d. 10 parts of Active Substance No. 6; 3 parts of a mixture of the sodium salts of saturated fatty alcohol sulphates; 5 parts of naphthalenesulphonic acid/formaldehyde condensate; 82 parts of kaolin.

The active substances are intimately mixed in suitable mixers with the additives, and the mixture is ground on the appropriate mills and rollers. There are obtained wettable powders that can be diluted with water to give suspensions of any desired concentration. Such suspensions can be used, for example, to treat cotton crops so that desiccation of the foliage occurs.

Emulsifiable concentrates

The following substances are used to produce (a) a 10% and (b) a 25% emulsifiable concentrate:

a. 10 parts of Active Substance No. 2; 3.4 parts of epoxidised vegetable oil; 3.4 parts of a combination emulsifier consisting of fatty alcohol polyglycol ether and alkylarylsulphonate calcium salt; 40 parts of dimethylformamide; 43.2 parts of xylene;

b. 25 parts of Active Substance No. 9; 2.5 parts of epoxidised vegetable oil; 10 parts of an alkylarylsulphonate/fatty alcohol polyglycol ether mixture; 5 parts of dimethylformamide; 57.5 parts of xylene.

It is possible to obtain from such concentrates, by dilution with water, emulsions of any desired concentration. Such emulsions are suitable for application to the foliage of cotton plants, leguminosae, potato foliage, etc..

I claim:

1. An arylisothiocyanate compound of the formula I

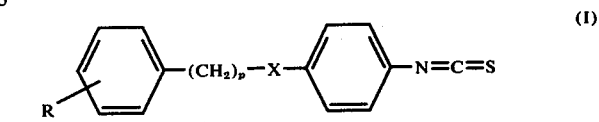

wherein
R represents hydrogen, lower alkyl, lower alkoxy or halogen,
X represents oxygen or sulphur, and
p represents an integer from 2 to 5.

2. The arylisothiocyanate compound according to claim 1 of the formula Ia

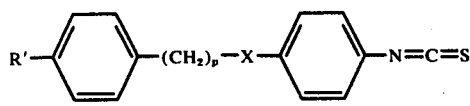 (Ia)

wherein
R' represents hydrogen, methyl, methoxy or halogen, and
p and X have the meanings given under the formula I.

3. As the compound according to claim 1, 4-(3'-phenyl-propoxy)-phenylisothiocyanate.
4. As the compound according to claim 1, 4-(2'-phenyl-ethylthio)-phenylisothiocyanate.
5. As the compound according to claim 1, 4-(4'-phenylbutoxy)-phenylisothiosyanate.
6. As the compound according to claim 1, 4-(5'-phenylpentyloxy)-phenylisothiosyanate.
7. A composition for the defoliation and desiccation of unlignified parts of plants above the soil, which composition comprises as active substance a defoliating and desiccating effective amount of an arylisothiocyanate according to claim 1, together with a suitable inert carrier therefor.
8. A process for the defoliation and desiccation of unlignified parts of plants above the soil, which process comprises applying thereto a defoliating and desiccating effective amount of an arylisothiocyanate according to claim 1.
9. The process of claim 8, wherein said arylisothiocyanate corresponds to the formula

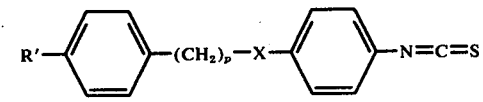

wherein R' represents hydrogen, methyl, methoxy or halogen, and p and X have the meanings given under the formula I.

* * * * *